(12) United States Patent
Den Boef et al.

(10) Patent No.: US 7,589,832 B2
(45) Date of Patent: Sep. 15, 2009

(54) INSPECTION METHOD AND APPARATUS, LITHOGRAPHIC APPARATUS, LITHOGRAPHIC PROCESSING CELL AND DEVICE METHOD

(75) Inventors: Arie Jeffrey Den Boef, Waalre (NL); Yevgeniy Konstantinovich Shmarev, Lagrangeville, NY (US)

(73) Assignee: ASML Netherlands B.V., Veldhoven (NL)

( * ) Notice: Subject to any disclaimer, the term of this patent is extended or adjusted under 35 U.S.C. 154(b) by 406 days.

(21) Appl. No.: 11/501,911

(22) Filed: Aug. 10, 2006

(65) Prior Publication Data

US 2008/0037134 A1 Feb. 14, 2008

(51) Int. Cl.
G01N 21/00 (2006.01)

(52) U.S. Cl. .................. 356/237.2; 356/237.5

(58) Field of Classification Search .... 356/237.1–237.5
See application file for complete search history.

(56) References Cited

U.S. PATENT DOCUMENTS

| | | | | |
|---|---|---|---|---|
| 5,631,773 A * | 5/1997 | Suzuki | | 359/562 |
| 5,703,692 A | 12/1997 | McNeil et al. | | 356/445 |
| 5,880,838 A | 3/1999 | Marx et al. | | 356/351 |
| 5,963,329 A | 10/1999 | Conrad et al. | | 356/372 |
| 6,091,075 A * | 7/2000 | Shibata et al. | | 250/559.44 |
| 6,608,690 B2 | 8/2003 | Niu et al. | | 356/635 |
| 6,624,894 B2 * | 9/2003 | Olszak et al. | | 356/511 |
| 6,699,624 B2 | 3/2004 | Niu et al. | | 430/5 |
| 6,704,661 B1 | 3/2004 | Opsal et al. | | 702/27 |
| 6,721,691 B2 | 4/2004 | Bao et al. | | 702/189 |
| 6,738,138 B2 | 5/2004 | Wei | | 356/369 |
| 6,753,961 B1 | 6/2004 | Norton et al. | | 356/364 |
| 6,768,983 B1 | 7/2004 | Jakatdar et al. | | 706/46 |
| 6,772,084 B2 | 8/2004 | Bischoff et al. | | 702/127 |
| 6,785,638 B2 | 8/2004 | Niu et al. | | 702/189 |
| 6,813,034 B2 | 11/2004 | Rosencwaig et al. | | 356/601 |
| 6,819,426 B2 | 11/2004 | Sezginer et al. | | 356/401 |
| 6,856,408 B2 | 2/2005 | Raymond | | 356/601 |
| 6,919,964 B2 | 7/2005 | Chu | | 356/601 |
| 6,928,628 B2 | 8/2005 | Seligson et al. | | 716/4 |
| 6,972,852 B2 | 12/2005 | Opsal et al. | | 356/625 |
| 6,974,962 B2 | 12/2005 | Brill et al. | | 250/548 |
| 6,987,572 B2 | 1/2006 | Lakkapragada et al. | | 356/601 |
| 7,046,376 B2 | 5/2006 | Sezginer | | 356/601 |
| 7,061,615 B1 | 6/2006 | Lowe-Webb | | 356/401 |
| 7,061,623 B2 | 6/2006 | Davidson | | 356/497 |
| 7,061,627 B2 | 6/2006 | Opsal et al. | | 356/601 |
| 7,068,363 B2 | 6/2006 | Bevis et al. | | 356/237.5 |
| 7,304,731 B2 * | 12/2007 | Hill | | 356/237.2 |
| 2004/0119970 A1 | 6/2004 | Dusa et al. | | 356/237.1 |
| 2006/0033921 A1 | 2/2006 | Den Boef et al. | | 356/446 |
| 2006/0066855 A1 | 3/2006 | Den Boef et al. | | 356/401 |
| 2006/0126074 A1 | 6/2006 | Van Der Werf et al. | | 356/489 |
| 2006/0139592 A1 | 6/2006 | Den Boef et al. | | 355/53 |
| 2006/0262297 A1 * | 11/2006 | Matsui et al. | | 356/237.5 |
| 2007/0052953 A1 * | 3/2007 | Hill | | 356/237.2 |

FOREIGN PATENT DOCUMENTS

| | | |
|---|---|---|
| EP | 1 628 164 A2 | 2/2006 |
| EP | 1 628 164 A3 | 4/2006 |

* cited by examiner

*Primary Examiner*—Michael P Stafira
(74) *Attorney, Agent, or Firm*—Sterne, Kessler, Goldstein & Fox P.L.L.C.

(57) ABSTRACT

In a scatterometry apparatus having an illumination aperture stop, a field stop is provided at an intermediate image to control the spot size on the substrate. The field stop may be apodized, e.g. having a transmissivity in the form of a trapezium or a Gaussian shape.

8 Claims, 2 Drawing Sheets

INSPECTION METHOD AND APPARATUS, LITHOGRAPHIC APPARATUS, LITHOGRAPHIC PROCESSING CELL AND DEVICE METHOD

FIELD

The present invention relates to a method of inspection usable, for example, in the manufacture of devices by a lithographic technique and to a method of manufacturing devices using a lithographic technique.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is desirable to measure one or more parameters of the patterned substrate, for example the overlay error between successive layers formed in or on it. There are various techniques for making measurements of the microscopic structures formed in a lithographic process, including the use of a scanning electron microscope and various specialized tools. One form of specialized inspection tool is a scatterometer in which a beam of radiation is directed onto a target on the surface of the substrate and one or more properties of the scattered or reflected beam are measured. By comparing the one or more properties of the beam before and after it has been reflected or scattered by the substrate, one or more properties of the substrate can be determined. This can be done, for example, by comparing the reflected beam with data stored in a library of known measurements associated with one or more known substrate properties. Two main types of scatterometer are known. A spectroscopic scatterometer directs a broadband radiation beam onto the substrate and measures the spectrum (intensity as a function of wavelength) of the radiation scattered into a particular narrow angular range. An angularly resolved scatterometer uses a monochromatic radiation beam and measures the intensity of the scattered radiation as a function of angle.

SUMMARY

In angle resolved scatterometry, the angle resolved spectrum is measured in the back focal plane of a high-NA lens. In many cases, for example thin film metrology or CD metrology of dense lines, the full back focal plane is illuminated. However, in other applications such as overlay metrology, no-overlapping diffraction orders in the back focal plane are required. This necessitates a special illumination mode, such as annular illumination, so that only a small portion of the back focal plane is illuminated. Such an illumination mode can be provided by inserting one or more blades or apertured plates in the illumination radiation path of the scatterometer.

However, if only a small part of the back focal plane is illuminated, the edge of the geometric spot on the substrate that is illuminated becomes broadened due to diffraction and radiation leaks out of the spot. This broadening, which is caused by diffraction, sets a lower limit on the target size. A small target is desirable to reduce the amount of space taken up by metrology targets and hence unavailable for device structures.

It is desirable, for example, to provide a scatterometer in which a special illumination mode can be used with a small target.

According to an aspect of the invention, there is provided an inspection apparatus configured to measure a property of a substrate, the apparatus comprising:
  a high-NA lens having a back focal plane;
  an illumination optical system configured to form an intermediate image of a radiation source and to project an image of the intermediate image onto a substrate through the high-NA lens, the illumination optical system having an illumination aperture blade which is imaged in the back focal plane;
  a detector arranged to measure an intensity of radiation in the back focal plane; and
  a field stop arranged at the intermediate image.

According to an aspect of the invention, there is provided a lithographic apparatus comprising:
  an illumination optical system arranged to illuminate a pattern;
  a projection optical system arranged to project an image of the pattern on to a substrate; and
  an inspection device configured to measure a property of a substrate, the inspection device comprising:
    a high-NA lens having a back focal plane;
    an illumination optical system configured to form an intermediate image of a radiation source and to project an image of the intermediate image onto a substrate through the high-NA lens, the illumination optical system having an illumination aperture blade which is imaged in the back focal plane;
    a detector arranged to measure an intensity of radiation in the back focal plane; and
    a field stop arranged at the intermediate image.

According to an aspect of the invention, there is provided a lithographic cell comprising:
  a coater arranged to coat a substrate with a radiation sensitive layer;
  a lithographic apparatus arranged to expose an image onto the radiation sensitive layer of the substrate coated by the coater;
  a developer arranged to develop an image exposed by the lithographic apparatus; and
  an inspection device configured to measure a property of a substrate, the inspection device comprising:
    a high-NA lens having a back focal plane;
    an illumination optical system configured to form an intermediate image of a radiation source and to project an image of the intermediate image onto a substrate through the high-NA lens, the illumination optical system having an illumination aperture blade which is imaged in the back focal plane;
    a detector arranged to measure an intensity of radiation in the back focal plane; and a field stop arranged at the intermediate image.

According to an aspect of the invention, there is provided a method of measuring a property of a substrate, comprising:

forming an intermediate image of a radiation source at a field stop using an illumination optical system containing an illumination aperture stop;

projecting an image of the intermediate image onto a substrate through a high-NA lens; and measuring the intensity of radiation reflected from the substrate in the back focal plane of the high-NA lens.

According to an aspect of the invention, there is provided a device manufacturing method comprising:

projecting an image of a device pattern and a reference pattern onto a radiation-sensitive layer of a substrate to form a device layer including device structures and a target pattern using a lithographic process;

forming an intermediate image of a radiation source at a field stop using an illumination optical system containing an illumination aperture stop;

projecting an image of the intermediate image onto the target pattern through a high-NA lens; and measuring the intensity of radiation reflected from the substrate in the back focal plane of the high-NA lens.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1A:
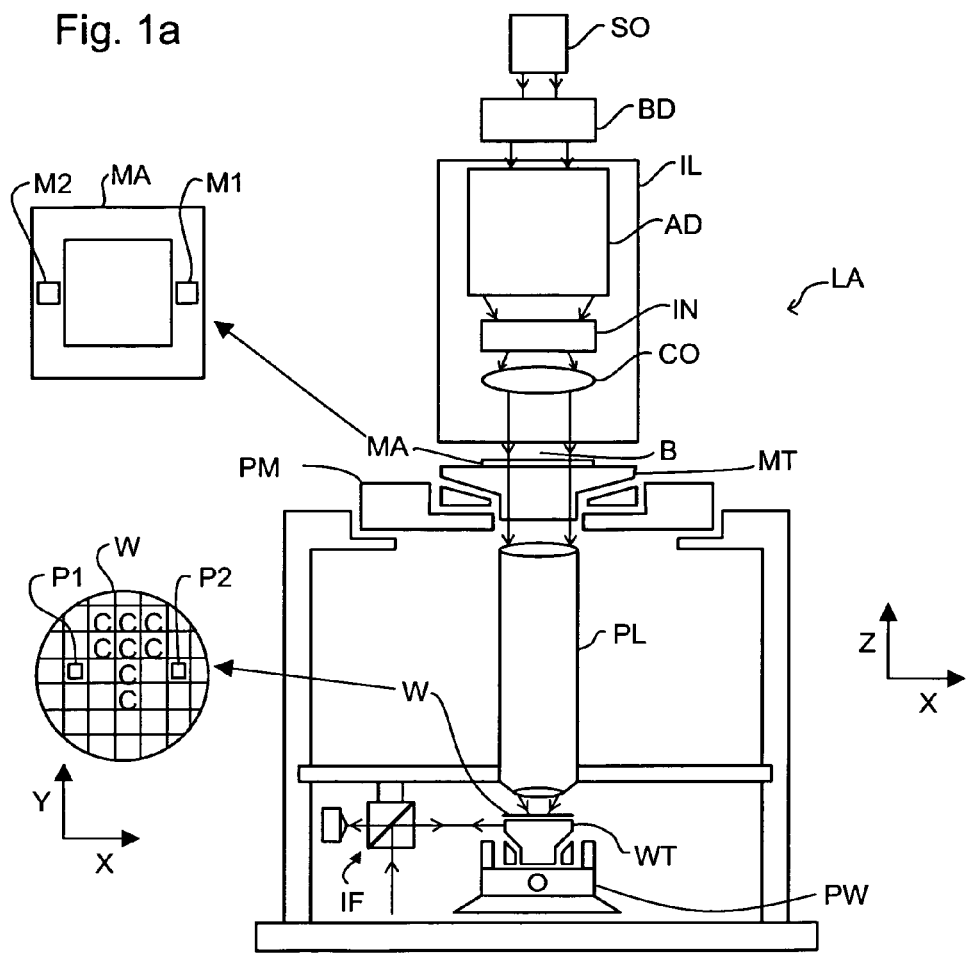
FIG. 1a depicts a lithographic apparatus.

FIG. 1a schematically depicts a lithographic apparatus. The apparatus comprises:

an illumination system (illuminator) IL configured to condition a radiation beam B (e.g. UV radiation or EUV radiation);

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more support structures). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1a, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device MA, the radiation beam B passes through the projection system PS, which focuses the beam onto a target portion C of the substrate W. With the aid of the second positioner PW and position sensor IF (e.g. an interferometric device, linear encoder or capacitive sensor), the substrate table WT can be moved accurately, e.g. so as to position different target portions C in the path of the radiation beam B. Similarly, the first positioner PM and another position sensor (which is not explicitly depicted in FIG. 1a) can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 1B:
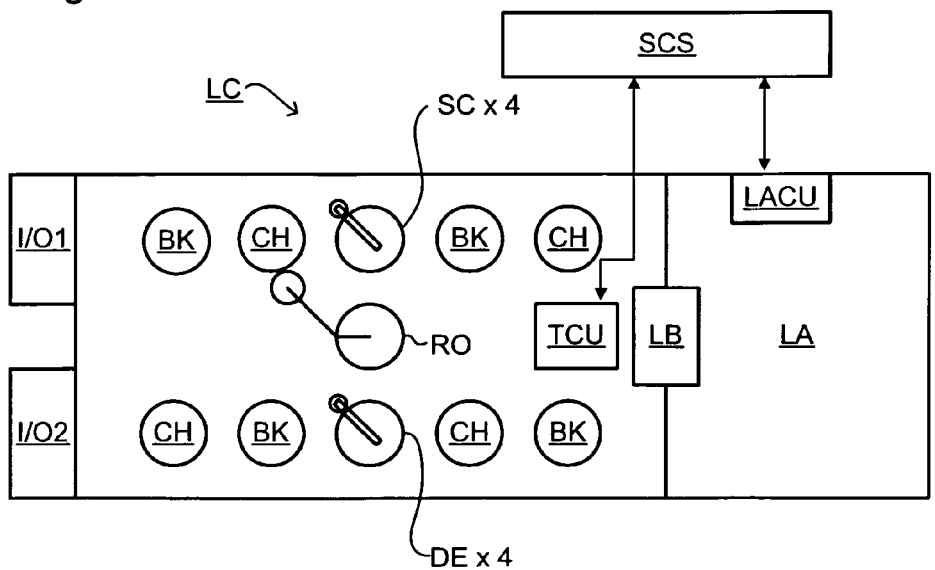
FIG. 1b depicts a lithographic cell or cluster.

As shown in FIG. 1b, the lithographic apparatus LA forms part of a lithographic cell LC, also sometimes referred to a lithocell or cluster, which also includes apparatus to perform one or more pre- and post-exposure processes on a substrate. Conventionally these include one or more spin coaters SC to deposit resist layers, one or more developers DE to develop exposed resist, one or more chill plates CH and one or more bake plates BK. A substrate handler, or robot, RO picks up substrates from input/output ports I/O1, I/O2, moves them between the different process devices and delivers them to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect an exposed substrate to measure one or more properties such as an overlay error between subsequent layers, line thicknesses, critical dimensions (CD), etc. If an error is detected, an adjustment may be made to exposure of one or more subsequent substrates, especially if the inspection can be done soon and fast enough that one or more other substrates of the same batch are still to be exposed. Also, one or more already exposed substrates may be stripped and reworked—to improve yield—or discarded—thereby avoiding performing exposure on a substrate that is known to be faulty. In a case where only some target portions of a substrate are faulty, further exposure can be performed only on those target portions which are good.

An inspection apparatus is used to determine the one or more properties of the substrate, and in particular, how one or more properties of different substrates or different layers of the same substrate vary from layer to layer. The inspection apparatus may be integrated into the lithographic apparatus LA or the lithocell LC or may be a stand-alone device. To enable rapid measurement, it is desirable that the inspection apparatus measure one or more properties in the exposed resist layer immediately after exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurement of the developed resist image—at which point either the exposed or unexposed parts of the resist have been removed—or after a pattern transfer step such as etching. The latter possibility limits the possibility for rework of a faulty substrate but may still provide useful information.

Figure 2:
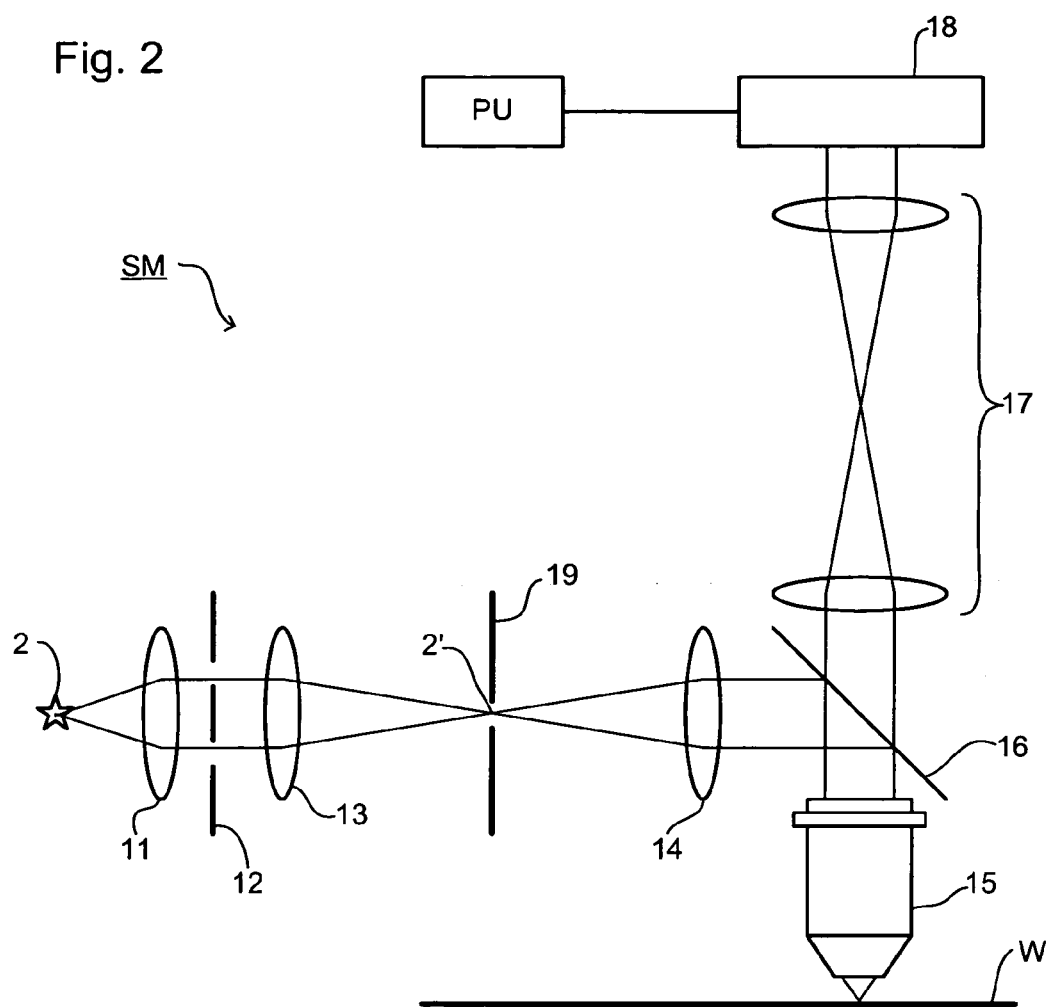
FIG. 2 depicts a scatterometer according to an embodiment of the invention.

FIG. 2 depicts a scatterometer according to an embodiment of the present invention. Radiation emitted by a radiation source 2 is collected by illumination system 11-14 and focused onto a spot covering a target on substrate W via a microscope objective lens 15 and partially reflective mirror 16. The microscope objective 15 has a high numerical aperture (NA), in an embodiment at least 0.9 or at least 0.95. An immersion scatterometer may even have a lens with a numerical aperture over 1. Radiation reflected by the substrate then transmits through partially reflective surface 16 into a detector 18 in order to have the scatter spectrum detected. The detector 18 is located in the back-projected pupil plane of the lens 15 or the pupil plane may instead be re-imaged with auxiliary optics 17 onto the detector 18. The pupil plane is the plane in which the radial position of radiation defines the angle of incidence and the angular position defines the azimuth angle of the radiation. The radiation source 2 may be part of the scatterometer or may simply be conduit of radiation from an outside radiation generator.

In an embodiment, the detector is a two-dimensional detector so that a two-dimensional angular scatter spectrum of the substrate target can be measured. The detector 18 may be, for example, an array of CCD or CMOS sensors, and may have an integration time of, for example, 40 milliseconds per frame.

The detector 18 may measure the intensity of scattered radiation at a single wavelength (or narrow wavelength range), the intensity separately at multiple wavelengths or the intensity integrated over a wavelength range. Furthermore, the detector may separately measure the intensity of transverse magnetic- and transverse electric-polarized radiation and/or the phase difference between the transverse magnetic- and transverse electric-polarized radiation.

Using a broadband radiation source (i.e. one with a wide range of radiation frequencies or wavelengths—and therefore of colors) is possible, which gives a large etendue, allowing the mixing of multiple wavelengths. The plurality of wavelengths in the broadband each has a bandwidth of *8 and a spacing of at least 2*8 (i.e. twice the wavelength). Several "sources" of radiation may be different portions of an extended radiation source which has been split using fiber bundles. In this way, angle resolved scatter spectra may be measured at multiple wavelengths in parallel. A 3-D spectrum (wavelength and two different angles) may be measured, which contains more information than a 2-D spectrum. This allows more information to be measured which increases metrology process robustness. This is described in more detail in European patent application publication EP1,628,164A.

The target on substrate W is selected so that it is sensitive to a parameter of the lithographic process to be investigated, for example, focus, dose or overlay. It may be a grating which is printed such that after development, the bars are formed of solid resist lines. The bars may alternatively be etched into the substrate. The scatterometry data of the printed grating can used by processing unit PU to reconstruct the target to derive from it a value for the parameter under investigation. One or more parameters of the ideal target, such as line widths and shapes, may be input to the reconstruction process from knowledge of the printing step and/or other scatterometry processes. Alternatively or additionally, information indicative of the parameter under investigation my derived directly from the scatterometry data, e.g. by a technique such as Principle Component Analysis.

The illumination system of the scatterometer SM can be regarded as formed of two parts: a first part, represented by lenses 11, 13, forms an intermediate image 2' of the radiation source 2, while a second part, represented by lens 14, working with the high-NA lens 15 images the intermediate image 2' onto the substrate W. An illumination aperture blade 12 is provided in the first part of the illumination system and is imaged into the back focal plane of the high-NA lens 15. The illumination aperture blade defines an illumination mode, for example annular illumination, suitable for the intended measurement, e.g. overlay.

Because the illumination aperture blade 12 blocks some of the spatial frequencies of the source 2, the image of the source on the substrate is broadened and radiation spills outside of the desired target area. Radiation reflected by structures outside the target area may cause noise in the scatterometry data. Therefore, a field stop 19 is provided at the intermediate image 2' of the radiation source 2. The field stop 19 is desirably only slightly larger than the ideal geometric spot width (e.g., diameter) and therefore blocks radiation that is diffracted outside the geometric spot, ensuring the spot projected onto the substrate is as sharp as possible.

Figure 3:
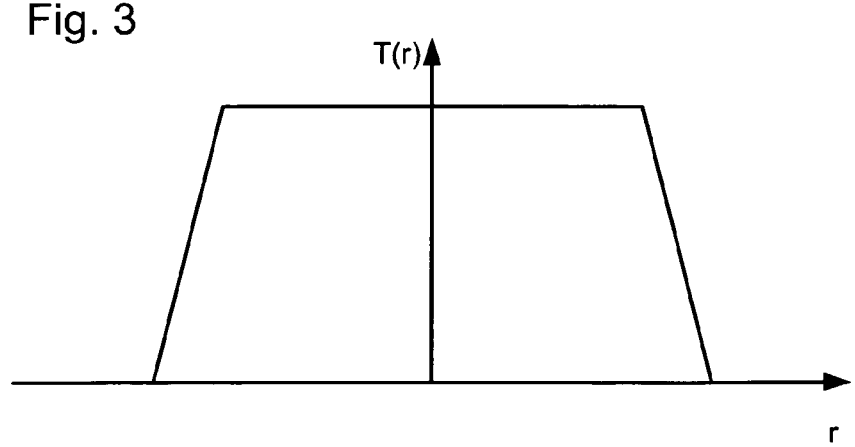
FIG. 3 depicts the transmittance of an apodized field stop used in an embodiment of the invention.

It is noted that the field stop 19 also acts as a low-pass filter for the image of the aperture blade 12 in the back focal plane of the high-NA lens 15, thus blurring the illumination mode. This may reduce the angular resolution of the diffraction orders on the detector 18. However, by using an apodized field stop, i.e. one in which the transition from transparent to opaque is gradual rather than step wise, an optimum balance between stray radiation in the image plane and angular resolution of the diffraction orders can be obtained. For example, a useful apodized field stop has a transmissivity T as a function of radius r along a diameter of the field stop that takes the form of a trapezium, as shown in FIG. 3. Other shapes, such as Gaussian, may also be used.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. An inspection apparatus configured to measure a property of a substrate, the apparatus comprising:
   a high-NA lens having a back focal plane and a longitudinal axis;
   an illumination optical system configured to form an intermediate image of a radiation source and to project an image of the intermediate image onto a substrate through the high-NA lens, the illumination optical system having an illumination aperture blade which is imaged in the back focal plane;
   a detector arranged along the longitudinal axis and configured to measure an intensity of radiation in the back focal plane, the measurement being used to determine at least one of an overlay error between successive layers of a substrate, line thickness and critical dimensions; and
   a field stop arranged at the intermediate image.

2. The inspection apparatus of claim 1, wherein the field stop is apodized.

3. The inspection apparatus of claim 2, wherein the transmissivity of the field stop along a width thereof has a trapezium shape.

4. The inspection apparatus of claim 2, wherein the transmissivity of the field stop along a width thereof has a Gaussian shape.

5. A method of measuring a property of a substrate, comprising:
   forming an intermediate image of a radiation source at a field stop using an illumination optical system containing an illumination aperture stop;
   projecting an image of the intermediate image onto a substrate through a high-NA lens having a longitudinal axis; and
   measuring the intensity of radiation reflected from the substrate along the longitudinal axis and in the back focal plane of the high-NA lens, the measuring being used to determine at least one of an overlay error between successive layers of a substrate, line thickness and critical dimensions.

6. The method of claim 5, wherein the field stop is apodized.

7. The method of claim 6, wherein the transmissivity of the field stop along a width thereof has a trapezium shape.

8. The method of claim 6, wherein the transmissivity of the field stop along a width thereof has a Gaussian shape.

* * * * *